US008864289B2

(12) United States Patent
Govyadinov et al.

(10) Patent No.: US 8,864,289 B2
(45) Date of Patent: Oct. 21, 2014

(54) DROP DETECTION

(75) Inventors: Alexander Govyadinov, Corvallis, OR (US); Chien-Hua Chen, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 0 days.

(21) Appl. No.: 13/985,393

(22) PCT Filed: Mar. 20, 2011

(86) PCT No.: PCT/US2011/029120
§ 371 (c)(1),
(2), (4) Date: Aug. 14, 2013

(87) PCT Pub. No.: WO2012/128749
PCT Pub. Date: Sep. 27, 2012

(65) Prior Publication Data
US 2013/0320198 A1   Dec. 5, 2013

(51) Int. Cl.
*B41J 2/125*   (2006.01)
*B41J 2/045*   (2006.01)
*G01V 8/16*   (2006.01)
*G01V 8/24*   (2006.01)
*B41J 2/165*   (2006.01)

(52) U.S. Cl.
CPC . *G01V 8/24* (2013.01); *B41J 2/125* (2013.01); *B41J 2/04856* (2013.01); *B41J 2/04561* (2013.01); *G01V 8/16* (2013.01); *B41J 2/04558* (2013.01); *B41J 2/16579* (2013.01)
USPC ........................................................... 347/81

(58) Field of Classification Search
USPC ..................... 347/73, 77, 78, 81, 82
See application file for complete search history.

(56) References Cited

U.S. PATENT DOCUMENTS

| 7,427,118 | B2 | 9/2008 | Mizes et al. |
| 2002/0158938 | A1 | 10/2002 | Doval |
| 2003/0193608 | A1 | 10/2003 | Yen |
| 2006/0139392 | A1 | 6/2006 | Fernandez et al. |
| 2009/0027459 | A1 | 1/2009 | Hawkins et al. |
| 2009/0244141 | A1 | 10/2009 | Govyadinov et al. |
| 2010/0020121 | A1 | 1/2010 | Mizes et al. |
| 2010/0177139 | A1 | 7/2010 | Na |

FOREIGN PATENT DOCUMENTS

| EP | 2145768 | 1/2010 |
| KR | 20070033197 | 3/2007 |
| WO | WO-2007015808 A1 | 2/2007 |

OTHER PUBLICATIONS

Taiwan Office Action (no translation), Case No. 101104187, dated Mar. 13, 2014, for PCT/US2011/029120, filed Mar. 20, 2011.

*Primary Examiner* — Kristal Feggins

(57) ABSTRACT

A drop detector assembly is provided including an ejection element to eject a fluid drop, a light guide to selectively receive light scattered off of the fluid drop, and a light detector formed in the light guide to detect light received by the light guide.

14 Claims, 6 Drawing Sheets

DROP DETECTION

BACKGROUND

An inkjet printer is a fluid ejection device that provides drop-on-demand ejection of fluid droplets through printhead nozzles to print images onto a print medium, such as a sheet of paper. Inkjet nozzles can become clogged and cease to operate correctly, and nozzles that do not properly eject ink when expected can create visible print defects. Such print defects are commonly referred to as missing nozzle print defects.

In multi-pass printmodes missing nozzle print defects have been addressed by passing an inkjet printhead over a section of a page multiple times, providing the opportunity for several nozzles to jet ink onto the same portion of a page to minimize the effect of one or more missing nozzles. Another manner of addressing such defects is speculative nozzle servicing in which the printer ejects ink into a service station to exercise nozzles and ensure future functionality, regardless of whether the nozzle would have produced a print defect. In single-pass printmodes, missing nozzle print defects have been addressed through the use of redundant nozzles on the printhead that can mark the same area of the page as the missing nozzle, or by servicing the missing nozzle to restore full functionality. However, the success of these solutions, particularly in the single-pass printmodes, relies on a timely identification of the missing nozzles.

BRIEF DESCRIPTION OF THE DRAWINGS

The present embodiments will now be described, by way of example, with reference to the accompanying drawings, in which.

DETAILED DESCRIPTION

Figure 1:
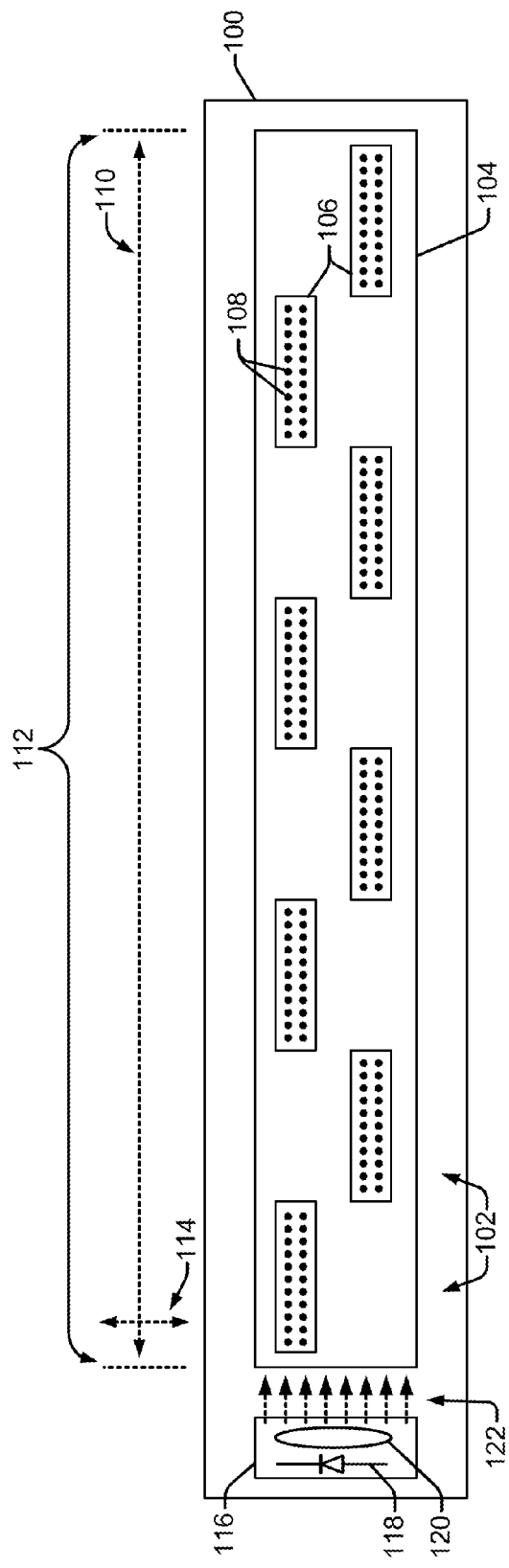
FIG. 1 is a bottom view of an example fluid ejection device suitable for incorporating a drop detector assembly as disclosed herein, according to an embodiment of the invention.

As noted above, the success of different solutions to missing nozzle print defects in inkjet printers relies on a timely identification of the missing nozzles. This is particularly true in single-pass printmodes, such as in page-wide array printing devices, where the option of passing the inkjet printhead over a section of a page multiple times generally does not exist.

Emerging inkjet printing markets (e.g., high-speed large format printing) call for higher page throughput without a decrease in print quality. This performance is achievable through the use of significantly larger printheads and single-pass printing with page-wide array printers. A consequence of the single-pass, page-wide array printing approach, however, is that the traditional multi-pass printing solution is not available.

In single-pass, page-wide array printing, there is a significant increase in the number print nozzles being used, and a corresponding increase in the time and ink volume needed to keep the nozzles healthy. Solutions for missing nozzle print defects in single-pass print modes include the use of redundant nozzles, which are additional nozzles on the printhead that can mark the same area of the page as the missing nozzle, and servicing the missing nozzle to restore it to its full functionality.

In order for such solutions to missing-nozzle print defects to be effective in single-pass print modes, the missing nozzles must be identified in a timely manner. Even in multi-pass printing environments, transient nozzle defects can be an issue that generally are correctable only upon real-time detection. One technique used for identifying missing nozzles is a light scatter drop detect (LSDD) method. In general, the LSDD technique enables assessment of nozzle functionality by monitoring light scattered off of fluid drops ejected from the nozzles. The LSDD technique is a scalable, cost effective drop detection solution that identifies missing nozzles and allows the printer to correct for them before they result in a print defect. The LSDD technique enables the high page throughput and print quality performance needed in emerging high-speed printing markets utilizing single-pass printing and page-wide array printheads.

The present concepts improve upon prior light scattering drop detect (LSDD) techniques by integrating light detectors with light guides on the printhead silicon die. The light detectors are arrayed in a manner that enables the capture of an optical signal (i.e., scattered light) corresponding to the presence or absence of fluid drops ejected by inkjet nozzles. The light guides may be configured to couple a light detector with scattered light from drops ejected by an adjacent nozzle or nozzles, but to reject scattered light from drops ejected by other nozzles. Light intensity detected by the light detectors will vary with distance from the light-scattering drop. Accordingly, where plural light detectors are employed, the light detectors may be used to determine the position of a drop from a particular nozzle, as well as the presence or absence of such drop.

Integrated light detectors and light guides, also referred to herein as drop detector assemblies, thus enable real-time drop/nozzle health detection and improved image printing quality for single-pass printers utilizing page-wide array printheads. However, the integrated light detectors and light guides may be used for image print quality improvement of multi-pass printers as well.

In some examples, the drop detector assembly includes an ejection element formed on a die substrate to eject a fluid drop. A light detector, also formed on the substrate, may be configured within a light guide to detect light scattered off of the ejected fluid drop. As described herein, the light guide may be configured to couple light scattered from drops ejected from a particular nozzle with a corresponding light detector. A detector circuit formed on the substrate is configured to provide indicator signals associated with the detected light, which indicates the presence and/or position of the ejected fluid drop.

The light detector and light guide may be protected by a transparent cover layer such that light scattered off of a fluid drop may be detected through the transparent cover layer. In some examples, the light guide may employ a lens, or other structure, to focus light on the light detector. Such a lens may enable greater signal differentiation by narrowing the acceptance angle of the light guide and/or may enhance efficient collection of light by increasing light intensity at the light detector.

In operation, an electronic controller may be used to control the ejection element and light detector. The light detector thus may be directed to detect light scattered off of the drop as the drop passes through a light beam. The method may include generating a drop, and indicator signals from associated light detectors when the drop is in a desired position. Where plural light detectors are employed, the indicator signals may be used to triangulate position of drops, for example, based on variations in intensity of light detected by two, three, four or more spaced light detectors.

FIG. 1 shows a bottom view of an example fluid ejection device 100 suitable for incorporating a drop detector assembly 102 as disclosed herein. In this example, the fluid ejection device 100 is an inkjet printer, such as a thermal or a piezo-electric inkjet printer, but other fluid ejection devices possible. Fluid ejection device 100 includes a printhead bar 104 that carries an array of print nozzles. The printhead bar 104 includes multiple printhead die 106 arranged in two staggered rows, and each die includes multiple individual print nozzles 108. The printhead bar 104 and array of print nozzles extend across the width 110 of a printzone 112 such that print media 222 (e.g., a sheet of paper; see FIG. 3) can move past the array of nozzles in a perpendicular direction 114 with respect to the width 110 of the printzone 112.

Each print nozzle 108 is configured to eject ink in a sequenced manner to cause characters, symbols, and/or other graphics or images to be printed on the print media 222 as it moves relative to the stationary printhead bar 104 in the perpendicular direction 114. Accordingly, in this example, fluid ejection device (inkjet printer) 100 can be referred to as a page-wide array printer having a fixed or stationary printhead bar 104 and array of print nozzles. However, although inkjet printer 100 is generally described herein as being a page-wide array printer, it is not limited to being a page-wide array printer, and in other examples it may be configured, for example, as a scanning type inkjet printing device.

Fluid ejection device 100 also includes a light source 116, such as a collimated light source. Light source 116 may be a light emitting diode 118 or a laser, for example, and it may include optics or a collimator 120 such as a lens or curved mirror. Light source 116 is configured to project a beam of light 122 across the array of print nozzles 108 in printhead bar 104 in the space between the nozzles and the print media 222. However, the light source may be positions elsewhere. Furthermore, although any shape of light beam 122 may be used, a rectangular cross-sectional shaped light beam 122 is shown in the described examples for the purpose of illustration (e.g., see FIG. 3).

Light source 116 generally functions in conjunction with and/or as part of a drop detector assembly 102 to provide light that scatters off of ejected fluid drops, into light guides and onto light detectors, as discussed below. Although only a single light source 116 is illustrated and discussed, different examples can include additional light sources depending, for example, on the power of the light source, the intensity of light needed to provide adequate scatter of light off of fluid drops ejected from nozzles 108, and so on.

Figure 2:
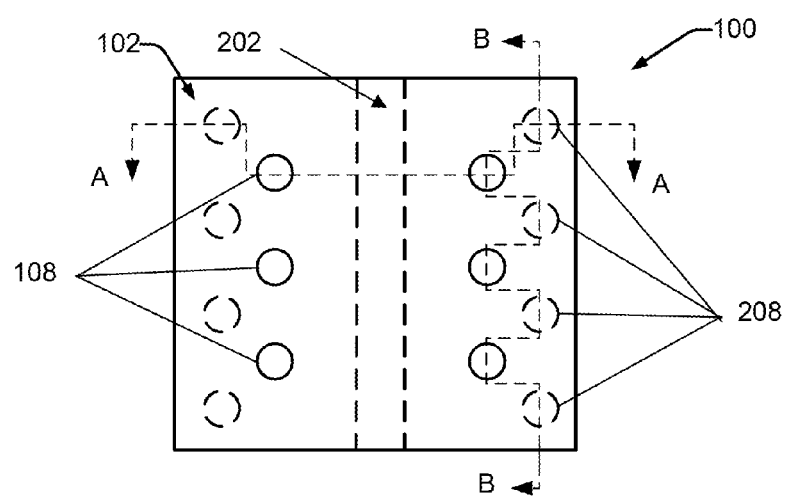
FIG. 2 is a top plan view of a drop detector assembly as shown in FIG. 2, according to an embodiment of the invention.

FIG. 2 is a top plan view showing a fluid ejection device 100 including an example drop detector assembly 102. As indicated, the fluid ejection device 100 includes a plurality of nozzles 108 arranged on opposed sides of a fluid slot 202. Drop detector assembly 102 employs a plurality of light guides 208 configured to couple corresponding light detectors 214 (FIGS. 3 and 4) with an adjacent nozzle or nozzles so as to provide for determination of drop position, as well as drop presence/absence.

Although FIG. 2 depicts a pair of light guides 208 flanking each nozzle 108, other arrangements may be employed. For example, two, three, four or more nozzles may surround each nozzle so as to provide for independent triangulation of position for drops expelled from each nozzle based. Similarly, a single group of light guides may be associated with two or more nozzles so as to provide for triangulation of drops expelled from any of a plurality of nozzles (regardless of source of the drops). As will be explained further, triangulation of drops may be based on the disparate light intensity received by the light detectors 214 (FIGS. 3 and 4) associated with the various light guides.

Figure 3:
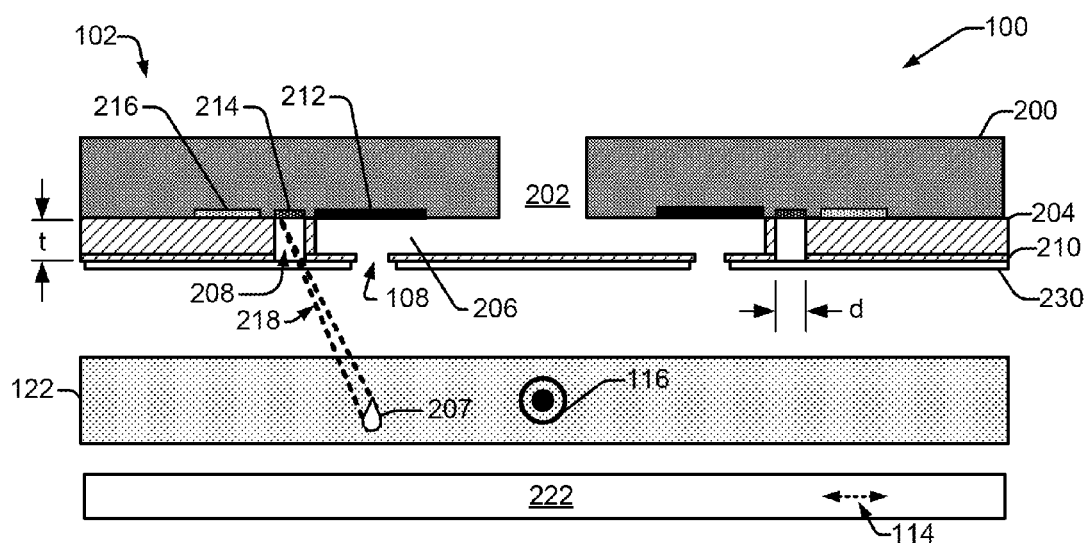
FIG. 3 is an offset side cross-sectional view of a drop detector assembly, according to an embodiment of the invention, the section being taken generally along line A-A of FIG. 2.

FIG. 3 is an offset side cross-sectional view showing an example drop detector assembly 102. FIG. 3 is taken generally along lines A-A of FIG. 2. Although the nozzles 108 appear (in FIG. 3) to be within the same plane as the light guides 208 (and light detectors 214), the nozzles 108 are actually offset from the nozzles 108 (as indicated generally by line A-A of FIG. 2).

As shown, drop detector assembly 102 may form a part of fluid ejection device 100, which in turn includes a die substrate 200 with a fluid slot 202 formed therein. The fluid slot 202 is an elongated slot that extends into the plane of FIG. 3, and is in fluid communication with a fluid supply (not shown), such as a fluid reservoir. Substrate 200 may take the form of a silicon die substrate that can be formed, for example, from Si wafers using standard micro-fabrication processes that are well-known to those skilled in the art (e.g., electroforming, laser ablation, anisotropic etching, sputtering, dry etching, photolithography, casting, molding, stamping, and machining). Therefore, substrate 200 can include features such as the fluid slot 202.

A chamber layer 204 is disposed on the substrate 200, the chamber layer defining ejection chambers 206 formed therein to contain ejection fluid (e.g., ink) from fluid slot 202 prior to the ejection. In the present example, chamber layer 204 also defines light guides 208 adjacent ejection chambers 206. Each light guide 208 may be within a range of approximately 10 micrometers to approximately 1000 micrometers from an adjacent ejection chamber 206. More typically, light guides will be between approximately 50 micrometers and approximately 250 micrometers from adjacent ejection chambers.

A nozzle plate 210 is disposed over the chamber layer 204 and forms the tops of ejection chambers 206. The nozzle plate 210 includes nozzles 108 through which fluid drops are ejected, and may further include openings corresponding to light guides 208. The chamber layer 204 may be formed, for example, of SU8 material, which provides suitable characteristics for guiding light along the light guides 208. As shown in FIG. 3, the light guides may be characterized by an opening with a diameter d that is less than the depth of the light guide (corresponding to the thickness t of channel layer 204). Light guides with an opening diameter that is less than the light guide depth will have a light acceptance angle that is suitable for detecting drops from an adjacent ejection chamber, but not for detecting drops from more distant ejection chambers.

In the present example, the light guides are sealed by a transparent cover layer 230, typically a layer of photo-imagable material such as SU8. In other examples, a transparent nozzle plate may seal the light guides. By covering the light guide, fluid may be prevented from entering the light guide, thereby improving light guide operation and enhancing effectiveness of surface cleaning.

As shown, an ejection element 212 is provided to eject a fluid drop 207 out of chamber 206 and through a corresponding nozzle 108. The ejection element 212 can be any device capable of operating to eject fluid drops 207 through nozzle 108, such as a thermal resistor or piezoelectric actuator. In the present example, ejection element 212 is a thermal resistor formed of a thin film stack fabricated on top of the substrate 200 (at the bottom of chamber 206). The thin film stack generally includes an oxide layer, a metal layer defining the ejection element 212, conductive traces, and a passivation layer (not individually shown).

Drop detector assembly 102 also includes a light detector 214 disposed within light guide 208, beneath transparent cover layer 230. Light detector 214 can be, for example, a photodetector, a charge-coupled device (CCD), or other similar light sensing devices. In the present example, light detector 214 is fabricated on the die substrate 200 (at the bottom of light guide 208). Light guide 208 generally is configured to receive light scattering off of a fluid drop 207 within an expected field of an associated nozzle, but to reject light scattering off of fluid drops outside of that expected field. The light detector thus may generate an electrical signal that is representative of the presence (or absence) of a drop within a particular light detector's field of view. Drop position and/or trajectory also may be determined based on the light intensity detected by the light detector, or by a group of light detectors.

A detector circuit 216 may be associated with each light detector 214 and also may be formed on substrate 200 to support each light detector 214. The drop detector assembly 102 also may include timing and bus circuitry (not shown), which facilitates timing for the capture of scattered light through the detector circuits 216, and for the readout of data from the detector circuits.

The light source 116 projects a light beam 122 toward the viewer and out of the plane of FIG. 2. In the present example, the light source may be selected to produce light on the order of 780 nanometers, 850 nanometers or 950 nanometers, which wavelengths have been shown to be suitable for use in an SU8 material light guide. As noted above, the illustrated light beam 122 has a rectangular cross-sectional shape. The light beam 122 travels the length of printhead bar 104 across the array of print nozzles 108 in the space between the nozzles 108 and the print media 222 (the print media 222 travels in a perpendicular direction 114 relative to the light beam 122 and printhead bar 104 (FIG. 1)).

As an ejected fluid drop 207 travels through the light beam 122, light is scattered off the drop 207 and scatters toward light detector assembly 102. Some of the scattered light (generally shown by dotted arrows 218) penetrates through the transparent cover layer 230, travels along light guide 208 and is absorbed or captured by light detector 214. Because of light guide 208, light detector 214 detects light scattered by drops ejected from adjacent nozzles, but does not detect light scattered by drops ejected from more remote nozzles. This may be due to the light acceptance angle of light guide 208, and/or due to loss of light though absorption (or refraction) of light at side walls of the light guide.

It is apparent that in order to maximize capture of scattered light from a fluid drop 107, light guides 208 may be located close to the associated nozzle 108. Although the light guides 208 (and light detectors 214) appear (in FIG. 3) to be on substrate 200 in a position that is within the same plane as nozzles 108, they are actually somewhat behind the nozzles 108 (i.e., set into the plane of FIG. 3) in a position that is closer to the light source 116 than the nozzles 108.

Figure 4:
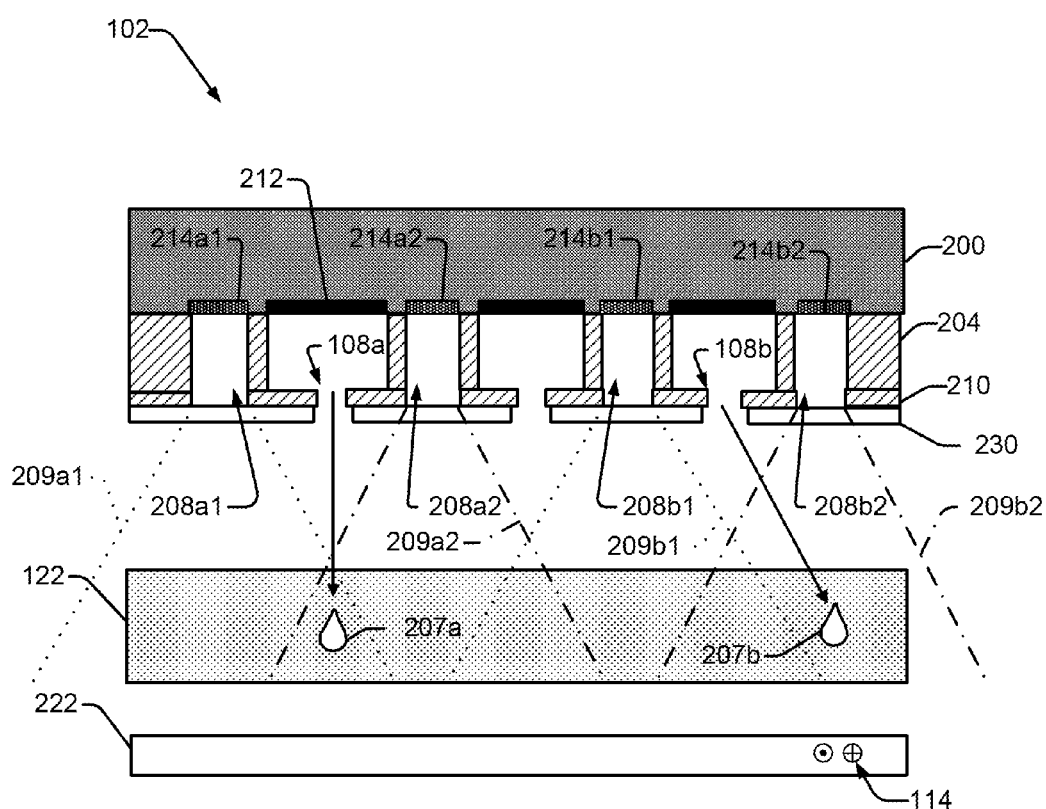
FIG. 4 is an offset cross-sectional view of a drop detector, according to an embodiment of the invention, the section being taken generally along line B-B of FIG. 2.

FIG. 4 is an offset side cross-sectional view taken generally along lines B-B of FIG. 2. Although the nozzles 108 appear (in FIG. 4) to be within the same plane as the light guides 208 (and light detectors 214), the nozzles 108 are actually offset from the nozzles 108 (as indicated generally by line B-B of FIG. 2). As indicated in FIG. 2, the view of the detector assembly 102 shown in FIG. 4 is generally orthogonal with respect to the view of the detector assembly 102 shown in FIG. 3. This view is intended to illustrate drop position detection using a set of light detectors operatively coupled to a selected nozzle. Although two light detectors are shown in each illustrated set, three or more light detectors (each with a distinct field of view) similarly may be employed to triangulate position of a drop. Furthermore, light detectors may operate as a part of one, two, or more distinct light detector sets. In other words, each light detector may be associated with more than one nozzle.

As noted above, light detectors 214 are fabricated on substrate 200, and thus are positioned underneath both the nozzle plate 210 and the chamber layer 204. The light detectors also are positioned beneath transparent cover layer 230. The detector 214 may be implemented using standard CMOS process steps, and in one example, the process uses a high resistivity substrate.

In general, light detectors 214 are arrayed along the length of substrate 200 such that they provide for maximum capture of optical signal (i.e., scattered light) upon proper ejection of a fluid drop. This may be accomplished using light guides to define a field of view for each light detector, providing for effective coupling of each light detector to a particular nozzle or nozzles. When a drop is in the field of view of a light detector, the corresponding light detector will detect scattered light from the drop. When a drop is outside the field of view of a light detector, the corresponding light detector will not detect scattered light from the drop.

In FIG. 4, light guide 208a1 defines a field of view 209a1 such that a drop 207a properly ejected from nozzle 108a will be detected by light detector 214a1. Correspondingly, light guide 208a2 defines a field of view 209a2 such that drop 207a also will be detected by light detector 214a2. Although each light detector has a broader field of view, the light detectors have a collective field of view (where field of view 209a1 and field of view 209a2 overlap) that is indicative of a properly ejected drop. In other words, only a properly ejected drop will be detected by both light detector 214a1 and light detector 214a2. The position of a properly ejected drop thus may be detected by drop detector assembly 102.

Position of an improperly ejected drop also may be detected by drop detector assembly 102. As indicated in FIG. 4, drop 207b improperly ejected from nozzle 108a will be detected by light detector 214b2, but will not be detected by light detector 214b1. This is because drop 207b is in the field of view 209b2 of light detector 214b2, but is not within the field of view 209b1 of light detector 214b1. Furthermore, the position drop 207b may be determined to be below light detector 214b2 based on the fact that scattered light is detected by light detector 214b2, but not by light detector 214b1. Position detection may be further refined by employing an additional light detector (or light detectors) to provide a more precise collective field of view (e.g., in a direction perpendicular to the plane of FIG. 4). Drop position (or trajectory) also may be extrapolated based on the light intensity received by the various light detectors.

Figure 5A:
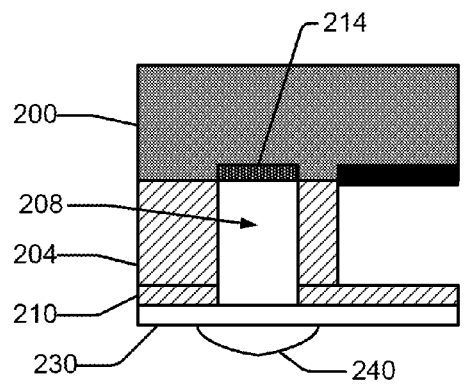
FIG. 5A is a fragmentary side cross-sectional view of a light guide of a drop detector assembly, the light guide employing a lens, according to an embodiment of the invention.

In some examples, a lens may be formed adjacent the light guide so as to narrow the light guide acceptance angle of the light guide, and/or to increase light intensity at the light detector within the light guide. FIG. 5A depicts a light guide with a convex lens 240 formed adjacent the entrance to light guide 208. More particularly, lens 240 is formed on the surface of cover layer 230 in the area covering light guide 208. Where a transparent nozzle plate is used as a transparent cover layer to cover light guide 208, the lens may be formed on the nozzle plate.

The depicted lens 240 may be formed by a process involving dry film lamination of a polymer material such as SU8 onto the exterior surface of cover layer 230, photo exposure and development of the polymer material, reflow of the developed polymer material to shape the lens, and UV and oven cure of the of the reflowed material. This process will result in a plano convex lens 240 as shown in FIG. 5A.

Lens 240 also may be formed by pin transfer of a polymer material such as SU8 onto the exterior surface of cover layer 230, reflow of the polymer material to shape the lens, and UV and oven cure of the of the reflowed material. This process also will result in a plano convex lens 240 as shown in FIG. 5A.

Figure 5B:
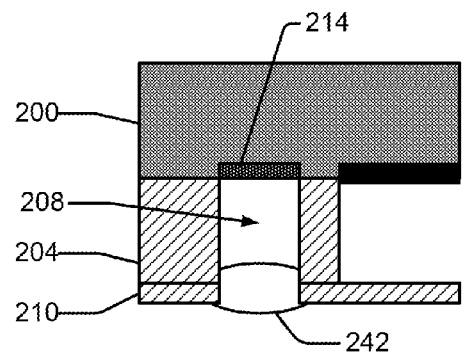
FIG. 5B is a fragmentary side cross-sectional view of a light guide of a drop detector assembly, the light guide employing a lens, according to an embodiment of the invention.

In some examples, a lens 242 may be formed within (or partially within) the light guide, as shown in FIG. 5B. This may be accomplished by pin transfer of a polymer such as such as SU8 into the light guide, reflow of the polymer material to shape the lens, and UV and oven cure of the of the reflowed material. The resulting lens may itself serve to cover the light guide, eliminating the need for a separate cover layer.

Figure 6:
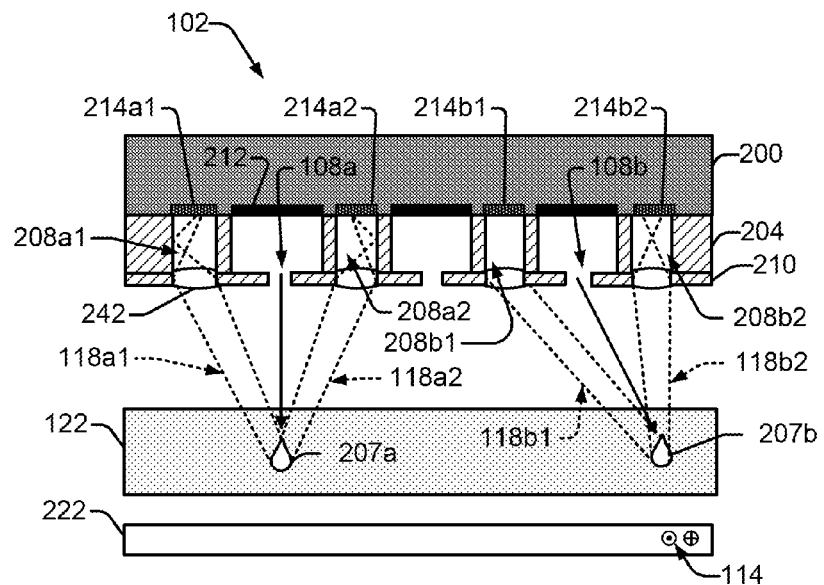
FIG. 6 is an offset cross-sectional view of a drop detector with light guides employing a lens, according to an embodiment of the invention, the section being taken generally along line A-A of FIG. 3.

Referring now to FIG. 6, a drop 207a that is properly ejected by nozzle 108a may effect scattered light 118a1 and 118a2 when passing through light beam 122. Such scattered light may be collected via lens light guides 208a1 and 208a2, and delivered to light detectors 214a1 and 214a2, respectively. Lens 242 (and/or lens 240) may be used to narrow the light guide acceptance angle of the light guide, and/or to increase light intensity at the light detector, thereby increasing signal strength.

As indicated, received light is reflected by the sidewalls of the respective light guides 208a1, 208a2, and focused on the respective light detectors 214a1, 214a2. Light reflected by light guide sidewalls will be partially absorbed depending on the incident angle, but not enough to entirely dissipate light entering from the light detector's field of view (as defined by the light guide and lens).

Light intensity will vary predictably with distance from the light detector (within the limits of each light detector's field of view), making it possible to triangulate position of a drop using detected intensity at plural light detectors. For example, position within the plane of FIG. 6 may be determined for a drop ejected by nozzle 108a based on light intensity at a pair of adjacent light detectors 214a1, 214a2. Additional light detectors may be employed to determine position in a plane perpendicular to the plane of FIG. 6.

An improperly ejected drop 207b (ejected from nozzle 108b) may be outside the field of view of an associated light detector, meaning that the light detector will not detect presence of the drop. This is illustrated in FIG. 6 by scattered light 118b1, which approaches light guide at an angle which will not be passed by the associated lens (or will substantially entirely dissipate by reflection off of the light guide sidewalls, and thus does not reach light detector 214b1. However, scattered light 118b2 will pass more directly into light guide 208b2, and thus will experience less dissipation of light than would scattered light from a properly ejected drop (due to decreased reflection off of the light guide sidewalls and/or due to a lower acceptance angle of light). Correspondingly, light detector 214b2 will detect a light intensity which indicates a more direct path of scattered light. Position of drop 207b within the plane of FIG. 6 thus still may be detected.

Figure 7:
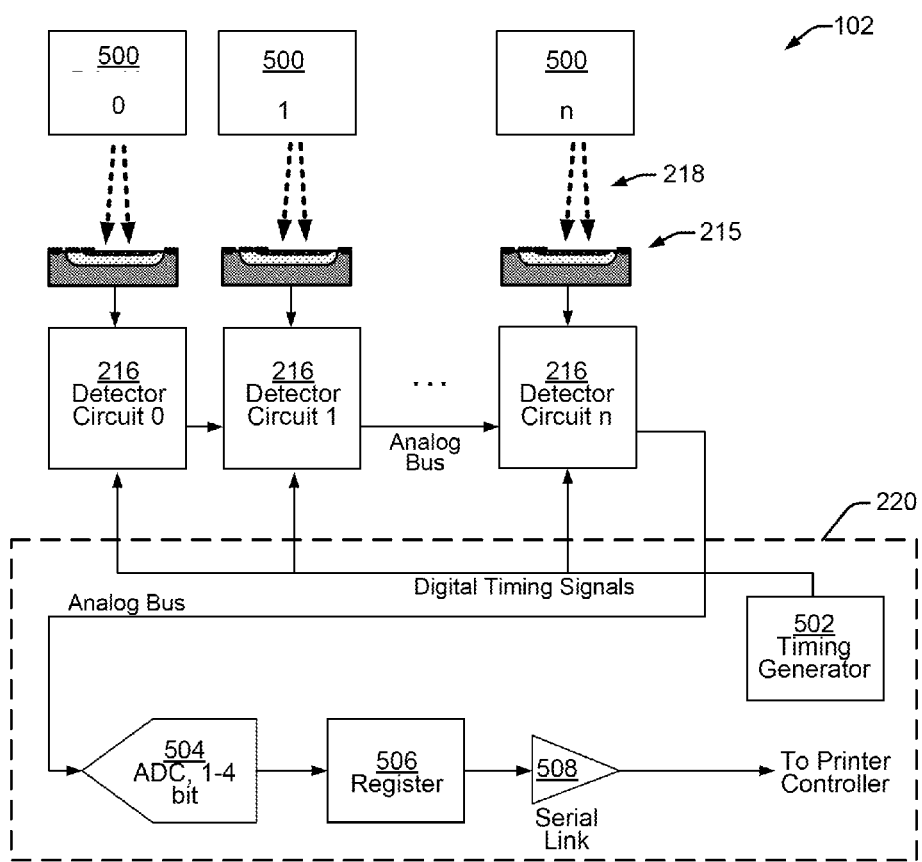
FIG. 7 shows a general block diagram of a drop detector assembly, according to an embodiment of the invention.

FIG. 7 shows a general block diagram of a drop detector assembly 102, where light detectors and light guides are arranged around nozzle groups (which may, but will not necessarily, take the form of a primitive). For each nozzle group 500 in assembly 102, there is a corresponding light detector array 215 and detector circuit 216, all formed on printhead die substrate 200. Timing and bus circuitry 220 is also formed on the die substrate 200. Each group 500 represents, for example, a group of nozzles 108 and related circuitry for controlling the drop ejection function of the nozzles. Timing generator 502 provides timing signals to control when and how long each detector circuit 216 integrates photocurrent from a corresponding light detector array 215 as the detectors capture or absorb light 218 scattered off of a fluid drop. Timing generator 502 controls the photocurrent integration time based on print data 608 (FIG. 8) from a printer controller 600 (FIG. 8) that informs the timing generator 502 which nozzle 108 in which group 500 is ejecting a fluid drop at a given moment. During the integration period, the detector circuit 216 integrates photocurrent and transforms it into a voltage. The timing generator 502 then reads out the voltage from the detector circuit 216 onto an analog bus. Thus, at an appropriate time when a nozzle 108 in a particular group 500 ejects a fluid drop, the timing generator 502 resets the appropriate detector circuit 216, begins and ends an integration period for the detector circuit 216, and reads out the voltage from the detector circuit 216 onto the analog bus.

The timing generator 502 also times and controls the placement of the output voltage from each detector circuit 216 onto the analog bus. Each voltage placed on the analog bus is converted by an analog-to-digital-converter 504 (ADC) into a digital value. The digital value from each detector circuit 216 is placed in register 506, and transmitted to the printer controller 600 through serial link 508. By collecting and monitoring scattered light 218, or a lack thereof, at appropriate times corresponding to when the ejection of fluid drops is expected (i.e., through correlation with print data from printer controller 600), a determination can be made as to whether a nozzle 108 is ejecting fluid drops. Thus, a determination can be made as to whether a nozzle is clogged, for example, in real time. In addition, the information gathered from the scattered light 218 can also enable determinations regarding the position, size and quality of a fluid drop, which can indicate the level of health in a nozzle. For example, this information can indicate whether a nozzle may be partially clogged. The printer controller 600 or printer writing system, for example, can then take corrective action to cover up for degraded or non-working print nozzles, such as by using print defect hiding algorithms.

Figure 8:
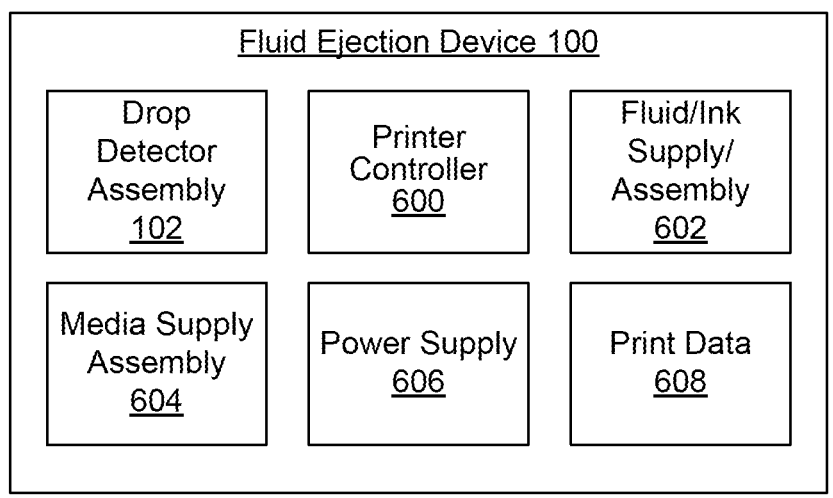
FIG. 8 shows a block diagram of a basic fluid ejection device, according to an embodiment of the invention.

FIG. 8 shows a block diagram of a basic fluid ejection device 100, according to an example. The fluid ejection device 100 includes drop detector assembly 102 and an electronic printer controller 600. Drop detector assembly 102 generally includes a fluid ejection assembly having additional drop detection elements that together make up drop detector assembly 102. Printer controller 600 typically includes a processor, firmware, and other electronics for communicating with and controlling drop detector assembly 102 to eject fluid droplets in a precise manner and to detect the ejection of the fluid drops.

In one example, fluid ejection device 100 is an inkjet printing device. As such, fluid ejection device 100 can also include a fluid/ink supply and assembly 602 to supply fluid to drop detector assembly 102, a media supply assembly 604 to provide media for receiving patterns of ejected fluid droplets, and a power supply 606. In general, printer controller 102 receives print data 608 from a host system, such as a computer. The print data 608 represents, for example, a document and/or file to be printed, and it forms a print job that includes one or more print job commands and/or command parameters. From the print data 608, printer controller 600 defines a pattern of drops to eject which form characters, symbols, and/or other graphics or images.

What is claimed is:

1. A drop detector assembly comprising:
   an ejection element to eject a fluid drop;
   a light guide to selectively receive light scattered off of the fluid drop;
   a lens formed adjacent the light guide to increase light intensity at the light detector upon receipt of scattered light from a fluid drop properly ejected by the ejection element; and
   a light detector formed in the light guide to detect light received by the light guide.

2. The drop detector assembly of claim 1, which further comprises a detector circuit to provide a signal associated with the detected light, the signal indicating a condition of the ejected fluid drop.

3. The drop detector assembly of claim 2, which further comprises a controller to control the ejection element, to determine the condition of the ejected fluid drop based on the signal, and to correlate the condition with the ejection element.

4. The drop detector assembly of claim 1, wherein the light guide has a field of view corresponding to receipt of scattered light from a fluid drop properly ejected by the ejection element.

5. A drop detector assembly as in claim 1, further comprising a light source to project a light beam to scatter light off of the fluid drop.

6. A drop detector assembly for determining position of an ejected fluid drop, the drop detector assembly comprising:
   a substrate;
   an ejection element formed on the substrate to eject the fluid drop;
   a light source to scatter light off of the fluid drop;
   a first light guide formed on the substrate adjacent the ejection element to selectively receive light scattered off of the fluid drop when the fluid drop is within a corresponding first field of view;
   a first light detector formed in the first light guide to detect light received by the first light guide;
   a second light guide formed on the substrate adjacent the ejection element to selectively receive light scattered off of the fluid drop when the fluid drop is within a corresponding second field of view; and
   a second light detector formed in the second light guide to detect light received by the light guide.

7. The drop detector assembly of claim 6, wherein the first field of view and the second field of view overlap to define a collective field of view.

8. The drop detector assembly of claim 7, wherein a properly ejected fluid drop passes through the collective field of view.

9. The drop detector assembly of claim 6, wherein the first light guide is on a first side of the ejection element and the second light guide is on a second side of the ejection element.

10. The drop detector assembly of claim 9, wherein the first light guide accepts light scattered from fluid drops positioned on the first side of the ejection element, but rejects light scattered from fluid drops positioned on the second side of the ejection element.

11. The drop detector assembly of claim 10, wherein the second light guide accepts light scattered from fluid drops positioned on the second side of the ejection element, but rejects light scattered from fluid drops positioned on the first side of the ejection element.

12. The drop detector assembly of claim 6, which further comprises a lens in each of the first light guide and the second light guide to focus received light respectively on the first light detector and second light detector.

13. A drop detector assembly comprising:
   a substrate having a chamber layer formed thereon, the chamber layer defining an ejection chamber with an ejection element formed therein to eject a fluid drop;
   a light source to scatter light off of the ejected fluid drop;
   light guides formed in the chamber layer adjacent the ejection chamber, the light guides having different overlapping fields of view from which the light guide accepts light scattered off of the fluid drop;
   light detectors formed in the light guides to detect light received by the light guides, intensity of the detected light being indicative of distance from the fluid drop to provide for triangulation of position of the fluid drop.

14. The drop detector assembly of claim 13, which further comprises a detector circuit to provide a signal associated with the detected light, and a controller to control the ejection element and to determine position of the ejected fluid drop based on the signal.

* * * * *